(12) United States Patent
Dubé

(10) Patent No.: US 10,871,492 B2
(45) Date of Patent: Dec. 22, 2020

(54) METHODS FOR LABELING URINE IN A SUBJECT WITH FLUOROPHORES

(71) Applicant: Mark Dubé, Sudbury (CA)

(72) Inventor: Mark Dubé, Sudbury (CA)

(73) Assignee: UPTRU INC., Sudbury (CA)

( * ) Notice: Subject to any disclaimer, the term of this patent is extended or adjusted under 35 U.S.C. 154(b) by 301 days.

(21) Appl. No.: 15/761,961

(22) PCT Filed: Sep. 21, 2016

(86) PCT No.: PCT/CA2016/051100
§ 371 (c)(1),
(2) Date: Mar. 21, 2018

(87) PCT Pub. No.: WO2017/049391
PCT Pub. Date: Mar. 30, 2017

(65) Prior Publication Data
US 2018/0284122 A1    Oct. 4, 2018

Related U.S. Application Data

(60) Provisional application No. 62/221,413, filed on Sep. 21, 2015.

(51) Int. Cl.
| G01N 21/64 | (2006.01) |
| G01N 33/58 | (2006.01) |
| G01N 33/94 | (2006.01) |
| G01N 33/493 | (2006.01) |

(52) U.S. Cl.
CPC ....... *G01N 33/582* (2013.01); *G01N 21/6428* (2013.01); *G01N 33/94* (2013.01); *G01N 33/493* (2013.01)

(58) Field of Classification Search
CPC ............... G01N 21/64; G01N 21/6428; G01N 21/6439; G01N 33/493; G01N 33/582; G01N 33/94; Y10T 436/142222
USPC ....... 436/63, 164, 172, 93; 422/82.05, 82.08
See application file for complete search history.

(56) References Cited

U.S. PATENT DOCUMENTS

| 3,089,815 | A | * | 5/1963 | Kupelwieser | ........ A61K 9/0019 514/774 |
| 3,917,812 | A | * | 11/1975 | Woog | ................. A61K 49/0091 435/19 |
| 4,953,562 | A | * | 9/1990 | Rosen | .................... G01N 33/82 436/56 |
| 5,039,616 | A | * | 8/1991 | Copelan | ............... A61B 5/1171 436/56 |
| 5,179,027 | A | * | 1/1993 | Fisher | ................. G01N 33/493 422/547 |
| 6,068,981 | A |   | 5/2000 | Rittenburg et al. | |
| 9,766,257 | B1 | * | 9/2017 | Hall | ..................... G01N 21/645 |
| 2006/0057728 | A1 |   | 3/2006 | Katz et al. | |
| 2014/0342380 | A1 |   | 11/2014 | Saal | |
| 2015/0369794 | A1 |   | 12/2015 | Keller | |

OTHER PUBLICATIONS

Winter et al. Annals of Emergency Medicine, vol. 19:6, Jun. 1990, pp. 663/71-667/75.*
Wallace et al. Annals of Emergency Medicine, vol. 38:1, Jul. 2001, pp. 49-54.*
Barry, R.E. et al., "Studies on the pharmocokinetics of fluorescein and its dilaurate ester under the conditions of the fluorescein dilaurate test," Arzneimittelforschung. 35(3): 644-648 (1985).
Buffington, C.A.T. et al., "Excretion of fluorescein in the urine of women with interstitial cystitis," J Urol. 158(3): 786-789 (1997).
Huppertz, B. et al., "Urine labeling with orally applied marker substances in drug substitution therapy," Clin Chem Lab Med. 42(6): 621-626 (2004).
International Search Report and Written Opinion for International Application No. PCT/CA2016/051100, dated Dec. 5, 2016 (9 pages).
Trewick, A.L., Glucose interference in pancreolauryl test,: Ann Clin Biochem. 35: 274-278 (1998).
Barteselli et al., "Safety and efficacy of oral fluorescein angiography in detecting macular edema in comparison with spectral domain optical coherence tomography," Available in PMC Sep. 1, 2014, published in final edited form as: Retina, 33(8): 1574-1583 (2013) (18 pages).
Kwan et al., "Fluorescein angiography and adverse drug reactions revisited: the Lions Eye experience," Clinical and Experimental Ophthalmology, 34(1): 33-38 (2006).
Soldin and Mattison, "Sex Differences in Pharmacokinetics and Pharmacodynamics," Available in PMC May 5, 2013, published in final edited form as: Clin Pharmacokinet, 48(3): 1-23 (2009) (23 pages).
Wallace et al., "The safety of intravenous fluorescein for confocal laser endomicroscopy in the gastrointestinal tract," Aliment Pharmacol Ther. 31(5): 548-552 (2010).

* cited by examiner

*Primary Examiner* — Maureen Wallenhorst
(74) *Attorney, Agent, or Firm* — Clark & Elbing LLP

(57) ABSTRACT

A method for labeling urine in a subject using fluorophores is provided that allows for determining if a urine sample originates from the subject that accepted the administered fluorophore. The method discloses detection of the fluorophore in the urine sample with optical means. One suitable fluorophore is fluorescein sodium. The method may be suitable for ensuring that urine samples for drug, illicit substance or other substance tests are genuine.

16 Claims, 2 Drawing Sheets

Fluorescein

5-Carboxyfluorescein

6-Carboxyfluorescein

2',7'-Dichlorofluorescein diacetate

O'-(Carboxymethyl)fluoresceinamide

Eosin Y disodium salt

Fluorescein-O'-acetic acid

METHODS FOR LABELING URINE IN A SUBJECT WITH FLUOROPHORES

FIELD OF THE INVENTION

The invention relates to methods for labeling urine in a subject with fluorophores that allows for determining if a urine sample originates from the subject that accepted the administered fluorophore.

BACKGROUND

In the United States, it is estimated that 120 million urine screening tests are performed annually to detect recent substance use.[1] The use of this method became particularly widespread in 1988, when the U.S. government introduced the first Mandatory Guidelines for Federal Workplace Drug Testing Programs.[2] Currently, urine testing is used in a variety of context including substance use disorder treatment, research settings, the workplace, schools, in emergency medicine, and in the criminal justice system.[3] Urine testing remains the dominant method in use, since the sample can be acquired relatively easily, the analysis is affordable, and the technique has been used for many years resulting in a well-studied procedure with clear cut-offs and guidelines.[4]

Given the consequences of a positive urine test, it is not surprising that several methods of tampering with urine samples have been devised. W. H. Jaffe et al. classified the methods of tampering into three basic categories: in vivo adulteration, in vitro adulteration, and urine substitution. In vivo adulteration includes "flushing" and "detoxification" as well as consumption of large volumes of liquid.[5] In vitro adulteration includes dilution or the urine sample or the addition of masking agents to the urine sample. Most of these processes can be detected during collection, inspection and analysis of the sample.[3] In order to ensure that the urine sample is not a substitution, it is recommended that urine be collected under direct observation.[1] However, direct observation is at times not feasible in some settings.

There is therefore a need for a method of determining if a collected urine sample from a subject originates from the same subject in a method that could increase patient dignity and potentially decrease costs. It would be advantageous for this method to be easily implemented and result in confident assessments.

SUMMARY OF THE INVENTION

In one embodiment, the present invention provides for a method of labeling urine in a subject, the method comprising:
  administering one or more fluorophores to the subject at a time prior to miction,
  obtaining a urine sample from the subject, and
  detecting the presence of the one or more fluorophores in the urine sample.

In a further embodiment of the method outlined above, the method further comprises screening the urine sample for one or more drugs, illicit substances or other substances and/or measuring urine parameters.

In a further embodiment of the method or methods outlined above, the drugs are cannabinoids, cocaine, phencyclidine, opiates, amphetamines, oxycodone, benzodiazepines, barbiturates, propoxyphene, methaqualone, 3,4-methylenedioxymethamphetamine, anaesthetics, methadone, hallucinogens, inhalants, anabolic steroids, hydrocodone, beta agonists, beta blockers, and glucocorticoids.

In a further embodiment of the method or methods outlined above, the illicit substances are androgens including testosterone and other anabolic steroids or precursors, stimulants including caffeine, nutritional supplements including herbs and extracts, alcohol, nicotine, diuretics and masking agents.

In a further embodiment of the method or methods outlined above, the other substances are growth hormone and growth factors, erythropoietin and creatine.

In a further embodiment of the method or methods outlined above, the urine parameters are temperature, specific gravity, pH, osmolality, colour viewed with natural light, odour, amount of creatine, amount of ions, amount of trace metals, amount of proteins, amount of vitamins, amount of metabolic molecules and amount of haematopoietic cells.

In a further embodiment of the method or methods outlined above, the method comprises a preliminary step of inspection of the subject by an administrator for one or more signs of substance use, wherein the administrator determines to proceed with labeling urine in the subject.

In a further embodiment of the method or methods outlined above, the one or more fluorophores is non-toxic.

In a further embodiment of the method or methods outlined above, the one or more fluorophores is excreted unchanged in the urine sample or metabolized into one or more second compounds that is one or more second fluorophores and is excreted in the urine sample.

In a further embodiment of the method or methods outlined above, the one or more fluorophores is fluorescein, a derivative or a salt thereof.

In a further embodiment of the method or methods outlined above, the one or more fluorophores is fluorescein sodium.

In a further embodiment of the method or methods outlined above, the amount of each of the one or more fluorophores administered to the subject is from about 50 to about 100 mg.

In a further embodiment of the method or methods outlined above, the amount of each of the one or more fluorophores administered to the subject is about 100 mg.

In a further embodiment of the method or methods outlined above, the amount of each of the one or more fluorophores administered to the subject is from about 0.6 to about 1.2 mg/kg body weight of the subject.

In a further embodiment of the method or methods outlined above, the amount of each of the one or more fluorophores administered to the subject is about 1.2 mg/kg body weight of the subject.

In a further embodiment of the method or methods outlined above, the administering is oral administering.

In a further embodiment of the method or methods outlined above, the time prior to miction is from about 5 to about 30 minutes, preferably about 20 minutes.

In a further embodiment of the method or methods outlined above, the one or more fluorophores is detected in the urine sample with a spectrophotometer, ophthalmoscope equipped with a cobalt blue or equivalent filter, fluorometer, UV light source capable of exciting the fluorophore or any combination thereof.

In a further embodiment of the method or methods outlined above, the one or more fluorophores is detected in the urine sample with an ophthalmoscope equipped with a cobalt blue or equivalent filter.

In a further embodiment of the method or methods outlined above, the one or more fluorophores is dissolved in about 200 to about 500 mL of an aqueous solution prior to administration.

In a further embodiment of the method or methods outlined above, the one or more fluorophores is dissolved in about 300 mL of an aqueous solution prior to administration.

In another embodiment, the present invention provides for a method of labeling urine in a subject, the method comprising:
  administering fluorescein sodium to the subject at a time 10 minutes prior to miction;
  obtaining a urine sample from the subject; and
  detecting the presence of fluorescein sodium in the urine sample with an ophthalmoscope equipped with a cobalt blue optical filter.

DETAILED DESCRIPTION

Figure 1:
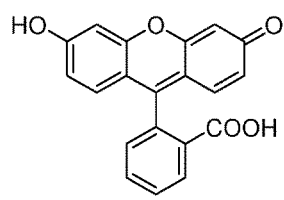
FIG. 1 represents the structure of fluorescein and examples of fluorescein derivatives or salts thereof.
Figure 1:
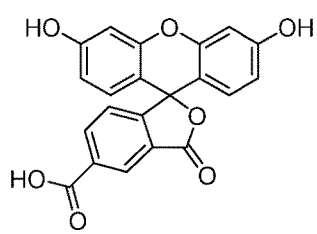
Figure 1:
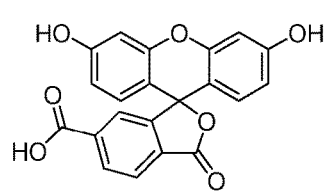
Figure 1:
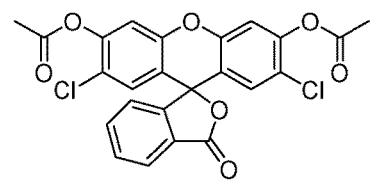
Figure 1:
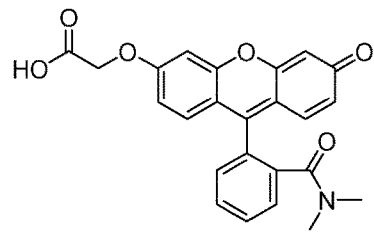
Figure 1:
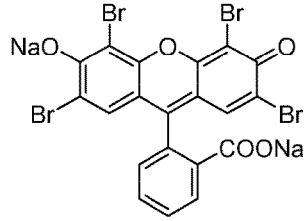
Figure 1:
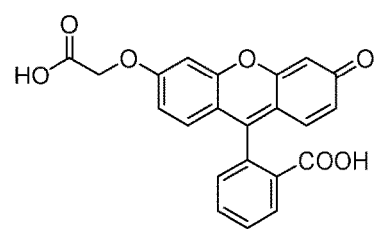

Described herein are methods for labeling urine in a subject. Also provided are methods of conducting a screening test, for example, but not limited to a drug, illicit substance or other substance screening test. Also provided is a method for testing a urine sample to determine if it originated from a specific subject. It will be appreciated that the methods and embodiments described herein are for illustrative purposes intended for those skilled in the art and are not meant to be limiting in any way. All references to embodiments or examples throughout the disclosure should be considered a reference to an illustrative and non-limiting embodiment or an illustrative and non-limiting example.

According to one embodiment of the present invention, there is provided a method of labeling urine in a subject, the method comprising:
  administering one of more fluorophores to the subject at a time prior to miction;
  obtaining a urine sample from the subject; and
  detecting the presence of the one or more fluorophores in the urine sample.

In the context of the present invention, by the term "miction" it is meant urination including elimination, sampling or voiding of urine from a subject voluntarily or otherwise.

The method may further comprise screening the urine for drugs, illicit substances or any other substances. It is contemplated that the screening for these drugs, illicit substances or any other substances may involve the detection of the metabolized forms of these compounds as would be produced in the human body. The detection of the drug, illicit substance or other substance in the original form is also contemplated. Determining if the metabolized form of the drug, illicit substance or other substance or of the original forms should be detected would be known to a person skilled in the art.

The types of drugs that can be screened for in the urine include, without limitation, cannabinoids, cocaine, phencyclidine, opiates, amphetamines, oxycodone, benzodiazepines, barbiturates, propoxyphene, methaqualone, 3,4-methylenedioxymethamphetamine, anaesthetics, methadone, hallucinogens, inhalants, hydrocodone, beta agonists, beta blockers, glucocorticoids, or any other drug that is excreted in the urine. The types of illicit substances that can be screened for in the urine include, without limitation, androgens including testosterone and other anabolic steroids or precursors, stimulants including caffeine, nutritional supplements including herbs and extracts, alcohol, nicotine, diuretics, masking agents or any other illicit substance. Other substances include, for example, but are not limited to, growth hormone and growth factors, erythropoietin, creatine or any other metabolite.

The method may further comprise screening for additional urine parameters, which may provide further data on the genuineness of the urine sample, including, without limitation, temperature, specific gravity, pH, osmolality, colour viewed with natural light, odour, amount of creatine, amount of ions and trace metals, amount of proteins, amount or vitamins, amount of metabolic molecules or amount of haematopoietic cells. Other parameters as are known in the art may also be included.

In a further embodiment, the method comprises a preliminary step of inspecting the subject by an administrator for one or more signs of substance use. These one or more signs of substance use include, for example, but not limited to, red eyes, runny nose, injection marks on arms or other areas of the body, sudden change in behaviour, mood swings, irritability, and/or changed sleeping pattern. Other signs of substance use may include, for example, but not limited to, enhanced physical performance, decreased physical performance, sudden change in appearance, lessening of pain, higher pain tolerance, or increased aggression. These signs may more readily indicate substance use by the subject, who may be more likely to replace or adulterate a urine sample in order to avoid detection. Many other signs of substance use may be detected, which will be apparent to the administrator and/or others. If the administrator detects these signs, the administrator may determine to proceed with labeling the urine in the subject to prevent the production of fraudulent urine samples.

It is contemplated that the fluorophore in the present invention is non-toxic. By "non-toxic" it is meant that the compound will not induce a harmful response to a majority of the population at the administered dose and is generally considered safe for oral consumption and/or intravenous administration.

It is also contemplated in the present invention that the fluorophore is excreted unchanged in the urine or metabolized into a second known compound that is also a fluorophore and excreted in the urine.

In the context of the present invention, detecting the presence of a fluorophore in the urine sample would indicate that the urine sample originates from the subject that accepted the administered fluorophore. In an embodiment where the urine is for the purpose of urine screening tests, a random administration of the fluorophore or a placebo may be contemplated. Although a subject could obtain the fluorophore to make a labeled urine sample for substitution, the subject would not know if the administered sample is expected to contain the fluorophore or not (i.e. if the subject had received the fluorophore or the placebo), particularly in cases where the composition comprising the fluorophore cannot be easily discerned from the placebo.

In another embodiment, more than one fluorophore can be administered. It therefore follows that the urine sample may comprise more than one fluorophore. This embodiment may also be particularly advantageous in the case of drug screening as administration of a randomized mixture of fluorophores increases the difficulty of successful urine adulteration. For example, from a selection of fluorophores A, B and C, eight separate samples may be prepared containing either an absence, one, two or three fluorophores each:

combination 1: no fluorophores;
combination 2: fluorophore A;
combination 3: fluorophore B;
combination 4: fluorophore C;
combination 5: fluorophores A and B;
combination 6: fluorophores A and C;
combination 7: fluorophores B and C; and
combination 8: fluorophores A, B and C.

There would only be a one in eight chance for a subject to guess the administered sample and adulterate the urine sample correctly.

In a further embodiment, a mixture of fluorophores can be administered at different ratios. This may result in the urine comprising the fluorophores at expected ratios. For example, from a selection of fluorophores A and B, many combination samples can be prepared. After administration of the sample, the urine sample is expected to comprise these fluorophores in a particular ratio.

In a further embodiment, it is contemplated that two different fluorophores may be administered which are known to have different clearance rates from the body into the urine. Thus, it will be appreciated that the urine sample may comprise a different ratio of fluorophores than in the administered sample. This would be expected as the fluorophores have different metabolic and bioavailability profiles affecting their excretion rate. The ratio may be known in advance or may be determined experimentally in a control group and compared to the fluorophore ratio found in the urine sample. This embodiment, in reference to urine drug screening tests, may impart another level of difficulty for subjects attempting urine substitution.

In one embodiment, the use of the present invention in the insurance industry is contemplated. Occasionally, insurance companies require urine samples to be produced wherein nicotine and/or proteins is detected, among other substances. The presence of these substances may affect insurance rates. As the collection of the urine sample is unwitnessed, the administration of a fluorophore prior to miction ensures the genuineness of the urine sample.

In a further embodiment, the detection of a fluorophore in the urine may be useful in genitourinary surgery. The surgeon may be alerted if an organ of the urinary tract has been breached by the visual appearance of the fluorophore during surgery. The fluorophore may be orally administered to the patient prior to surgery at a time determined to produce the most beneficial results or may be administered intravenously to the patient during surgery.

Any fluorophore that can be administered and excreted in the urine in a reasonable amount of time at a concentration enabling detection and that remains unchanged in the urine or metabolized into a second fluorophore is contemplated in the present invention. Without wishing to be limiting, one example of a fluorophore that can be used to label the urine of a subject is fluorescein or derivatives and salts thereof (see FIG. 1). The ability of fluorescein to fluoresce under a blue light source when in high dilution makes this fluorophore an attractive option for the purposes of the present invention. Some examples of fluorescein derivatives are presented in FIG. 1. Examples of fluorescein salts include, but are not limited sodium, potassium, iodide, amine, phosphate, phosphonium, pyridimium, or sulfate salts. These examples are meant to present a general idea fluorescein modifications and it is not necessarily suggested that these fluorescein derivatives may be suitable for use in the present invention.

A representative example of a fluorescein or derivatives and salt thereof is fluorescein sodium salt, depicted in formula (I). Fluorescein sodium salt, also known as oral fluorescein, is used extensively in health care applications, especially in fundus angiography, and is generally considered safe even up to a dose of 25 mg/kg of body weight.[6-10]

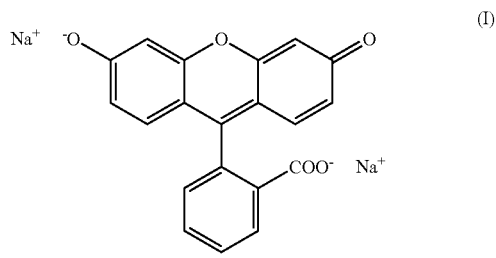

In one embodiment of the present invention, from about 50 mg to about 100 mg of the fluorophore is administered to the subject prior to miction, for example but not limited to 50, 55, 60, 65, 70, 75, 80, 85, 90, 95 or 100 mg. In a further embodiment, about 0.6 to about 1.2 mg of the fluorophore/kg body weight of the subject is administered, for example but not limited to 0.6, 0.8, 1.0 or 1.2 mg/kg body weight.

In a particularly preferred embodiment, the administration route is oral administration. This can be particularly efficient as an oral administration route does not require additional equipment such as disinfection solutions and syringes as well as training of personnel for intravenous administration or the like. However, in certain circumstances, intravenous administration is also possible.

It will be appreciated that the fluorophores may be in the form of a pill, tablet, capsule, liquid, solution, syrup, dispersion, suspension, powder or any other formulation which will enable the delivery of the fluorophore into the body of the subject. The fluorophores may be combined with aqueous solutions, for example, water, coffee, juice or other beverages, or may be combined with food.

The administration of the fluorophore at a certain time prior to miction is important in order to allow for the fluorophore to pass into the urine. A short duration time after administration but prior to miction may result in the fluorophore not passing into the urine while a long duration time may cause the fluorophore in the urine to be too dilute for detection. It should be understood that the optimal duration time will be dependent on a variety of factors, for example age, gender, weight, state of health, health of gastrointestinal tract, whether the fluorophore is administered in a fed or fasted state, gastric emptying rate, interactions with other foods/drugs and/or metabolic differences. In one embodiment of the present invention, the fluorophore is administered from about 5 to 30 minutes prior to miction. In another embodiment, the fluorophore is administered about 20 minutes prior to miction.

As fluorophores emit fluorescence upon excitation, the detection of the fluorophore in the urine sample can be performed with any device and/or means that will result in a positive result (i.e., the presence of the fluorescence). In particular, detection of the fluorophore encompasses exciting the fluorophore at a particular wavelength(s) and detecting and/or measuring the resulting fluorescence emission.

Detection also involves the ability to differentiate the presence of fluorescence from background/baseline interference.

Figure 2:
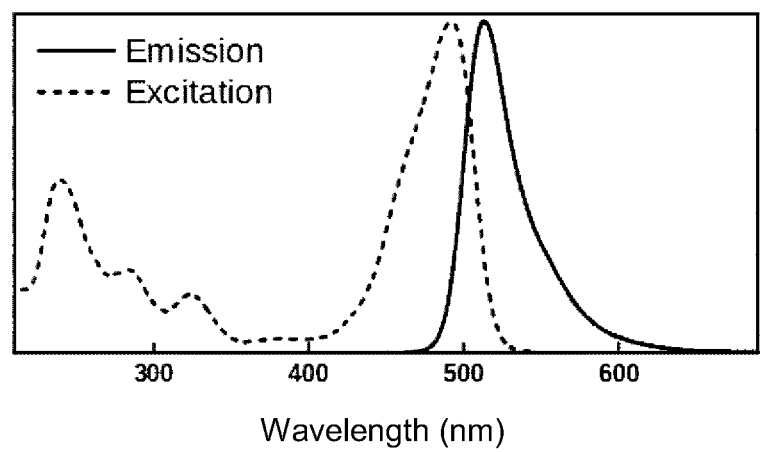
FIG. 2 is a representation of the excitation and emission profile of fluorescein.

An excitation and emission profile for fluorescein is show in FIG. 2. Peak excitation occurs at 494 nm and peak emission occurs at 521 nm. Any means of exciting the fluorescein is contemplated in the present invention. In one embodiment, a fluorometer is used to detect the fluorescence of fluorescein by exciting fluorescein at a suitable wavelength, for example 488 nm, and detecting the emitted fluorescence. In another embodiment, a opthalmoscope equipped with a cobalt blue filter is used to visualize fluorescein light emission. In this method, white light is passed through a cobalt blue filter which allows wavelengths of 390 to 410 nm to pass, exciting the fluorescein, and visually observing the green fluorescence. A cobalt blue filter greatly enhances viewing fluorescein sodium wherein almost 100% of the absorbed light is converted to green fluorescent light. In yet another embodiment, UV light is used to excite fluorescein. In particular, WA light is used, consisting of wavelengths ranging from 320 to 400 nm.

It is one aim of the present invention that an administered dose of the fluorophore will result in a high confidence of assessment. For example, it is contemplated that at a specific dose, close to 100% of urine samples will be interpreted as having fluorescence. A minimization of false-negatives is especially desirable as it relates to urine screening tests since it may be difficult to repeat the procedure.

In an embodiment where the fluorophores are for oral administration, the fluorophores are dissolved in about 100 to about 500 mL of an aqueous solution prior to administration, for example 100, 150, 200, 250, 300, 350, 400, 450 or 500 mL. In a further embodiment, the fluorophores are dissolved in about 300 mL of water prior to administration. In yet a further embodiment, it is contemplated that the fluorophore may be dissolved in, for example, 100 mL of an aqueous solution, administered to the subject, followed by the administration of an aqueous solution without the fluorophores, for example, 200-400 mL. For instance, the fluorophore is dissolved in 100 mL of coffee and administered to the subject. Directly following administration, the subject drinks an additional 200 mL of water.

In a further embodiment of the present invention there is provided a kit comprising one or more fluorophores in one or more solutions described herein.

Based on the disclosure provided above, there is provided a variety of embodiments which are not meant to be exhaustive or limiting in any manner. The embodiments described below are contemplated.

In one embodiment, there is provided a method of labeling urine in a subject, the method comprising:
administering one or more fluorophores to the subject in an amount of from about 50 to about 100 mg at a time prior to miction;
obtaining a urine sample from the subject; and
detecting the presence of the one or more fluorophores in the urine sample.

In another embodiment, there is provided a method of labeling urine in a subject, the method comprising:
administering one or more fluorophores to the subject in an amount of about 100 mg at a time prior to miction;
obtaining a urine sample from the subject; and
detecting the presence of the one or more fluorophores in the urine sample.

In another embodiment, there is provided a method of labeling urine in a subject, the method comprising:
administering one or more fluorophores to the subject in an amount of about 0.6 to about 1.2 mg/kg body weight of the subject at a time prior to miction;
obtaining a urine sample from the subject; and
detecting the presence of the one or more fluorophores in the urine sample.

In another embodiment, there is provided a method of labeling urine in a subject, the method comprising:
administering one or more fluorophores to the subject in an amount of about 1.2 mg/kg body weight of the subject at a time prior to miction;
obtaining a urine sample from the subject; and
detecting the presence of the one or more fluorophores in the urine sample.

In another embodiment, there is provided a method of labeling urine in a subject, the method comprising:
administering fluorescein sodium to the subject at a time prior to miction;
obtaining a urine sample from the subject; and
detecting the presence of fluorescein sodium in the urine sample with an opthalmascope equipped with a cobalt blue optical filter.

In another embodiment, there is provided a method of labeling urine in a subject, the method comprising:
administering fluorescein sodium to the subject at a time 20 minutes prior to miction;
obtaining a urine sample from the subject; and
detecting the presence of fluorescein sodium in the urine sample with an opthalmascope equipped with a cobalt blue optical filter.

In another embodiment, there is provided a method of labeling urine in a subject, the method comprising:
administering fluorescein sodium in an amount of about 50 to about 100 mg to the subject at a time 20 minutes prior to miction;
obtaining a urine sample from the subject; and
detecting the presence of fluorescein sodium in the urine sample with an opthalmascope equipped with a cobalt blue optical filter.

In another embodiment, there is provided a method of labeling urine in a subject, the method comprising:
administering fluorescein sodium in an amount of about 100 mg to the subject at a time 20 minutes prior to miction;
obtaining a urine sample from the subject; and
detecting the presence of fluorescein sodium in the urine sample with an opthalmascope equipped with a cobalt blue optical filter.

In another embodiment, there is provided a method of labeling urine in a subject, the method comprising:
administering fluorescein sodium in an amount of about 0.6 to about 1.2 mg/kg body weight of the subject to the subject at a time 20 minutes prior to miction;
obtaining a urine sample from the subject; and
detecting the presence of fluorescein sodium in the urine sample with an opthalmascope equipped with a cobalt blue optical filter.

In another embodiment, there is provided a method of labeling urine in a subject, the method comprising:
administering fluorescein sodium in an amount of about 1.2 mg/kg body weight of the subject to the subject at a time 20 minutes prior to miction;
obtaining a urine sample from the subject; and
detecting the presence of fluorescein sodium in the urine sample with an opthalmascope equipped with a cobalt blue optical filter.

In one embodiment, there is provided a method of labeling urine in a subject, the method comprising:
- inspecting the subject by an administrator for one or more signs of substance use, and when the one or more signs of abuse are detected;
- administering one or more fluorophores to the subject at a time prior to miction, obtaining a urine sample from the subject; and
- detecting the presence of the one or more fluorophores in the urine sample.

In another embodiment, there is provided a method of screening urine, the method comprising:
- administering or not administering one or more fluorophores to the subject at a time prior to miction;
- obtaining a urine sample from the subject; and
- detecting the presence of the one or more fluorophores in the urine sample if the one or more fluorophores is administered to the subject.

In another embodiment, there is provided a method of screening urine, the method comprising:
- inspecting the subject by an administrator for one or more signs of substance use, and when the one or more signs of abuse are detected;
- administering or not administering one or more fluorophores to the subject at a time prior to miction,
- obtaining a urine sample from the subject; and
- detecting the presence of the one or more fluorophores in the urine sample if the one or more fluorophores is administered to the subject.

Example

In a blind study, 50 mg of fluorescein was administered orally to a healthy male volunteer, followed by 350 mL of tap water. Urine was collected at 5 minute intervals for a total of 20 minutes. The samples were analyzed by one experienced, and one inexperienced observer with cobalt blue light from a standard Welch Allyn ophthalmoscope. The experiment was performed seven times, with more than 48 hour intervals between each experiment.

Figure 3:
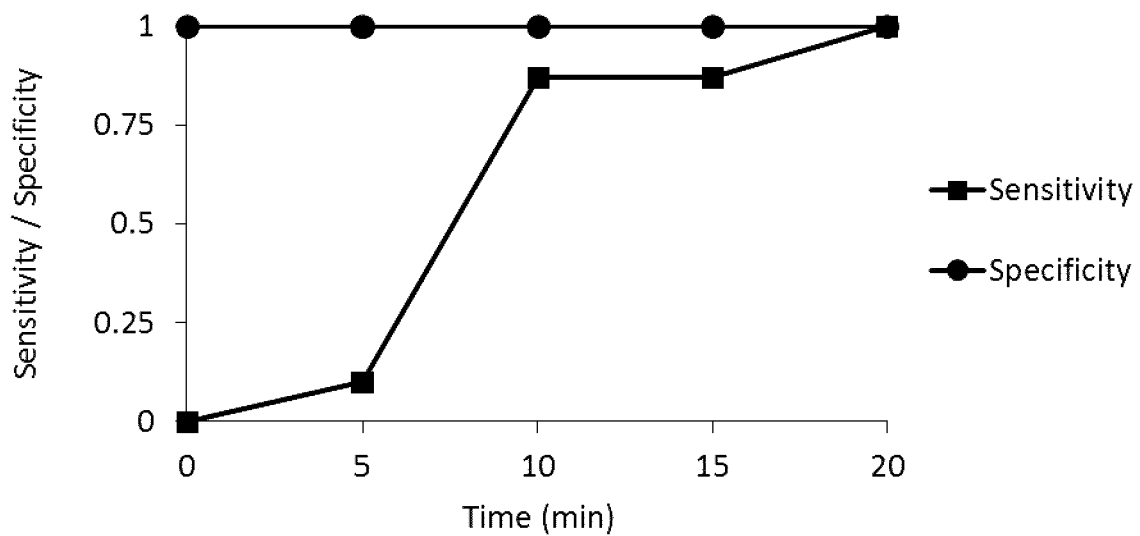
FIG. 3 represents the sensitivity and specificity of detecting fluorescein in a urine sample vs. time.

The results are presented in FIG. 3. There was no difference in the rate of detection of the fluorescein between the two observers. The sensitivity was 0.87 (confidence interval: 0.60-0.97) at 10 minutes and rose to 1.0 (confidence interval: 0.73-1.0) at 20 minutes. The specificity was 1.0 (confidence interval: 0.59-1.0) constantly.

While this invention has been particularly shown and described with references to embodiments thereof, it will be understood by those skilled in the art that various changes in from and details may be made. The scope of the claims should not be limited to the illustrative embodiments, but should be given the broadest interpretation consistent with the scope and spirit of the invention.

All documents are herein incorporated by reference in their entirety.

REFERENCES

1. Reynolds, L. A. Historical Aspects of Drugs-of-Abuse Testing in the United States. In *Drugs of abuse: body fluid testing*; Wong, R. C.; Tse H. Y., Eds.; Human Press Inc.: New Jersey, 2005, pp 1-10.
2. Lewis, J. H. *Drug detection and its role in law enforcement*. Trends and Issue in Crime and Criminal Justice, 205, 2001, pp 1-6.
3. Jaffee, W. B., Trucco, E., Levy, S., & Weiss, R. D. *Ensuring validity in urine drug screens and tests;* 2006. Manuscript submitted for publication.
4. *Urine Specimen Collection Handbook for Federal Agency Workplace Drug Testing Programs*, Nov. 1, 2004, Substance Abuse and Mental Health Services Administration.
5. Cone, E. J., Lange, R., and Darwin, W. D. In *vivo adulteration: excess fluid ingestion causes false-negative marijuana and cocaine urine test results*. Journal of Analytical Toxicology 1998, 22(6), 460-473.
6. Watson, A. P., and Rosen, E. S. *Oral fluorescein angiography: reassessment of its relative safety and evaluation of optimum conditions with use of capsules*. British Journal of Ophthalmology 1990, 74(8), 458-461.
7. Nayak, B. K.; Ghose, S. *A method for fundus evaluation in children with oral fluorescein*. British journal of ophthalmology 1987, 71(12), 907-909.
8. Barteselli, G.; et al. *Safety and efficacy of oral fluorescein angiography in detecting macular edema in comparison with spectral domain optical coherence tomography*. Retina 2013, 33(8), 1574.
9. Wallace, M. B.; et al. *The safety of intravenous fluorescein for confocal laser endomicroscopy in the gastrointestinal tract*. Alimentary Pharmacology & Therapeutics 2010, 31, 548-552.
10. Kwan, A. S. L.; Barry C.; McAllister, F.; Constable, I. *Fluorescein angiography and adverse drug reactions revisited: the Lions Eye experience*. Clinical and Experimental Opthalmology 2006, 34, 33-38.

What is claimed is:

1. A method of detecting fluorescently labelled urine from a subject, the method comprising:
   - orally administering an amount of fluorescein to the subject at a time prior to miction;
   - obtaining a urine sample from the subject; and
   - detecting fluorescence of the fluorescein in the urine sample, wherein the fluorescein is detected in the urine sample with an ophthalmoscope equipped with a cobalt blue or equivalent filter.

2. The method of claim 1, wherein the method further comprises screening the urine sample for one or more drugs, illicit substances or other substances and/or measuring urine parameters, and wherein the drugs are cannabinoids, cocaine, phencyclidine, opiates, amphetamines, oxycodone, benzodiazepines, barbiturates, propoxyphene, methaqualone, 3,4-methylenedioxymethamphetamine, anaesthetics, methadone, hallucinogens, inhalants, hydrocodone, beta agonists, beta blockers, and glucocorticoids, the illicit substances are androgens including testosterone, anabolic steroids, stimulants including caffeine, nutritional supplements including herbs and extracts, alcohol, nicotine, and diuretics, the other substances are growth hormone and growth factors, erythropoietin and creatine and the urine parameters are temperature, specific gravity, pH, osmolality, colour viewed with natural light, odour, amount of creatine, amount of ions, amount of trace metals, amount of proteins, amount of vitamins, and amount of haematopoietic cells.

3. The method of claim 1, wherein the method comprises a preliminary step of inspection of the subject by an administrator for one or more signs of substance abuse, wherein the administrator determines to proceed with labeling urine in the subject.

4. The method of claim 1, wherein the fluorescein is non-toxic.

5. The method of claim 1, wherein the fluorescein is excreted unchanged in the urine sample or metabolized into one or more second compounds that is one or more second fluorophores and is excreted in the urine sample.

6. The method of claim 1, wherein the fluorescein is a derivative or a salt thereof.

7. The method of claim 6, wherein the fluorescein is fluorescein sodium.

8. The method of claim 1, wherein the amount of fluorescein administered to the subject is from about 50 to about 100 mg.

9. The method of claim 8, wherein the amount of fluorescein administered to the subject is about 100 mg.

10. The method of claim 8, wherein the amount of fluorescein administered to the subject is about 50 mg.

11. The method of claim 1, wherein the amount of fluorescein administered to the subject is from about 0.6 to about 1.2 mg/kg body weight of the subject.

12. The method of claim 11, wherein the amount of fluorescein administered to the subject is about 1.2 mg/kg body weight of the subject.

13. The method of claim 1, wherein the time prior to miction is from about 5 to about 30 minutes.

14. The method of claim 13, wherein the time prior to miction is about 20 minutes.

15. The method of claim 1, wherein the fluorescein is dissolved in about 200 to about 500 mL of an aqueous solution prior to administration.

16. The method of claim 15, wherein the fluorescein is dissolved in about 300 mL of an aqueous solution prior to administration.

* * * * *